US006986952B2

(12) United States Patent
Itagaki et al.

(10) Patent No.: US 6,986,952 B2
(45) Date of Patent: Jan. 17, 2006

(54) CHEMICAL COMPOUND CAPABLE OF EMITTING VISIBLE LIGHT, AND LUMINESCENT MATERIAL, ELECTRO-LUMINESCENT DEVICE, AND DISPLAY APPARATUS THAT CONTAIN THE CHEMICAL COMPOUND

(75) Inventors: Youichi Itagaki, Atsugi (JP); Norio Hasegawa, Tochigi (JP)

(73) Assignee: Mitsumi Electric Co., Ltd., Tokyo (JP)

( * ) Notice: Subject to any disclaimer, the term of this patent is extended or adjusted under 35 U.S.C. 154(b) by 0 days.

(21) Appl. No.: 10/458,089

(22) Filed: Jun. 10, 2003

(65) Prior Publication Data
US 2004/0166363 A1    Aug. 26, 2004

(30) Foreign Application Priority Data
Jun. 14, 2002    (JP) ............................. 2002-174745

(51) Int. Cl.
*H05B 33/14*    (2006.01)
*C09K 11/06*    (2006.01)
*C07D 409/00*   (2006.01)

(52) U.S. Cl. ..................... 428/690; 428/917; 313/504
(58) Field of Classification Search ............... 428/690, 428/917; 313/504; 548/440; 549/59
See application file for complete search history.

(56) References Cited

U.S. PATENT DOCUMENTS
6,048,630 A * 4/2000 Burrows et al. ............ 428/690

FOREIGN PATENT DOCUMENTS
JP    62-244058    * 10/1987
JP    2001-085713  * 3/2001
JP    2003-129043  * 5/2003

OTHER PUBLICATIONS
Wu et al., Chemistry of Materials, 13(8), p. 2626-2631, (2001).*

* cited by examiner

*Primary Examiner*—Dawn Garrett
(74) *Attorney, Agent, or Firm*—Ladas and Parry LLP

(57) ABSTRACT

A chemical compound capable of emitting visible light and having electrical conductivity comprises a main chain that consists of at least one substituted or non-substituted 2,5-thiophenediyl group and at least one substituted or non-substituted 9-carbazolyl group that bonds to at least one of two terminals of the main chain. The chemical compound is used in a luminescent material, an EL device that includes a luminous layer, and a display apparatus that includes a plurality of EL devices.

7 Claims, 3 Drawing Sheets

CHEMICAL COMPOUND CAPABLE OF EMITTING VISIBLE LIGHT, AND LUMINESCENT MATERIAL, ELECTRO-LUMINESCENT DEVICE, AND DISPLAY APPARATUS THAT CONTAIN THE CHEMICAL COMPOUND

BACKGROUND OF THE INVENTION

1. Field of the Invention

The present invention generally relates to a chemical compound capable of emitting visible light and having electrical conductivity, a luminescent material that contains the chemical compound, an electro-luminescent device including a luminous layer that contains the chemical compound, and a display apparatus that includes a plurality of the electro-luminescent devices.

2. Description of the Related Art

It is expected for an electro-luminescent (EL) device to be utilized as display device elements for various display apparatuses or a light source for illumination such as a backlight, since luminescence with high brightness can be obtained from the EL device when even a low voltage is applied to the EL device. The EL device elementarily has a structure provided by laminating a transparent anode, one or more (typically, 3 through 5) layers that include a luminous layer, and a cathode from bottom to top, on a transparent glass or plastic substrate. When a voltage is applied between the anode and the cathode of the EL device, both holes from the anode and electrons from the cathode are injected into the luminous layer. Herein, the luminous layer contains a luminescent material that emits light by utilizing energy provided due to the recombination of the holes and the electrons.

Additionally, the plurality of the layers may include not only the luminous layer but also a hole-transporting layer for improving the injection efficiency of the holes or an electron-transporting layer for improving the injection efficiency of the electrons, or both of them that sandwich the luminous layer therebetween.

Also, an electro-luminescent (EL) display apparatus is one type of image display panel, in which a plurality of the above-mentioned EL devices are arranged, for forming an image by driving the EL devices as the pixels of the image. Particularly, in order to produce a full-color image display panel, it is necessary to arrange EL devices that emit light with one color of the three primary colors in the additive color process, that is, red, green, and blue lights, as the pixel of an image.

Now, the following three approaches for realizing the EL devices for emitting one of the three-color lights as described above have been suggested.

As the first approach, the luminous layer of the EL device that constitutes each pixel of an image and emits red light, green light, or blue light is formed from a luminescent material that is selected independently for each color and is different from the luminescent material for other colors. Each of the luminescent materials can generate red light, green light, or blue light, by utilizing energy provided due to the recombination of the holes and the electrons. Thus, the full color EL display apparatus having three-color pixels of an image can be produced.

As the second approach, first, the luminous layers of all the EL devices corresponding to all the pixels of an image are formed from one kind of luminescent material for emitting white light. The luminescent material for emitting white light emits white light that contains red light, green light, and blue light, by utilizing energy provided due to the recombination of the holes and the electrons. Secondly, color filers for transmitting red light, green light, or blue light are disposed on the surfaces of the EL devices as the pixels, through which white light is emitted. Thus, each of the three-color lights is extracted from the white light emitted from the EL device through the color filter for the corresponding color and the full color EL display apparatus having three-color pixels of an image can be produced.

As the third approach, all the EL devices corresponding to all the pixels of an image are formed from a luminescent material for emitting blue light. For pixels that emit red light or green light, a color conversion layer for converting blue light into red light or green light, respectively, is formed on the surface of the EL device that emits blue light. The luminescent material for emitting blue light generates blue light with comparatively high energy by utilizing energy provided due to the recombination of the holes and the electrons. Both color conversion layers for red light and for green light are photo-excited by the blue light with comparatively high energy generating from the luminescent material for emitting blue light and emit red light and green light, respectively. Thus, the full color EL display apparatus having three-color pixels of an image can be produced, from which the green light and the red light that are converted from the blue light as well as the blue light are emitted.

In the above-mentioned first approach that is most widely used at present, a luminescent material for one luminous color generally has a molecular structure quite different from luminescent materials for other colors. Accordingly, where the hole-transporting layer and/or the electron transporting layer are/is laminated on those luminous layers having molecular structures quite different from each other, the conditions for laminating a hole transporting layer and/or the electron transporting layer on the luminous layer for one color are also quite different from the conditions for other colors, dependent on the kinds of the luminous layers for respective colors. Thus, it is generally difficult to produce an EL display apparatus by employing such luminescent materials having molecular structures quite different from each other for respective colors.

As described above, since the molecular structure of a luminescent material for one color is quite different from that of luminescent materials for other colors, the service life of the luminescent material for one color is also different from service lives for the luminescent materials for other colors. That is, deterioration of the pixels for one color of the EL display apparatus is different from that of the pixels for other colors. Herein, the anodes and/or the cathodes of the EL display devices are usually common in some EL devices. Accordingly, EL devices corresponding to respective pixels are dependent on each other in the EL display apparatus, so that it is difficult to replace the EL device with a new one in one-pixel units. Thus, when the above-mentioned luminescent materials for respective colors with a service life quite different from each other are employed, it is difficult to replace an EL device for a luminous color that is made from a luminescent material with short service life with a new one independently, and there is included the disadvantage that the whole of the EL display apparatus has to be replaced with a new one.

As described above, when the EL display apparatus is produced according to the first approach, both the cost for producing the EL display apparatus and the cost for replacing the EL display device with a new one become high.

In the above-mentioned second approach, a common luminescent material for emitting white light is employed for the luminous layers of all the EL devices, so that the lamination conditions and the service lives for the luminescent materials are basically common among all the EL display devices. However, in the second approach, since the color filter acts to extract light with a wavelength in a specific spectral region from the white light, visible light other than the extracted light with the wavelength in the specific spectral region may be absorbed by the color filter. Accordingly, the efficiency of the utilization of the visible light relative to the generation of the white light is low and the loss of the energy of the white light is high.

Also, in the above-mentioned third approach, although a common luminescent material for emitting blue light is employed for the luminous layers of all the EL devices, for the EL devices for emitting red light or green light, the color conversion layers for red light or green light have to be laminated, so that the EL devices for emitting light with colors different from each other have to be produced in lamination structures different from each other.

Also, in the second approach, even if the intensities of the white lights emitted from the EL devices are approximately common, after the white lights transmit through the respective color filters provided on the EL devices, the intensities of the transmitted lights for the respective colors are generally different from each other. Also in the third approach, even if the intensities of the blue lights emitted from the EL devices are approximately common, generally, the intensities of both the green light and the red light emitted from the respective color conversion layers are quite different from the intensity of the blue light that is not converted by a color conversion layer. In addition, since the color conversion layer for red color is formed from a material different from that for the color conversion layer for green color, the quantum yield of the color conversion layer for red color is usually different from the quantum yield of the color conversion layer for green color, so that the intensity of the green light emitted from the color conversion layer for green color is different from the intensity of the red light emitted from the color conversion layer for red color. Accordingly, when an EL display apparatus is produced according to the second or third approach, it is necessary to control the luminous intensity for each color. However, it is generally difficult to greatly change the voltage applied between the anode and the cathode of the EL device for each color.

SUMMARY OF THE INVENTION

It is a general object of the present invention to provide a chemical compound capable of emitting visible light and having electrical conductivity, a luminescent material that contains the chemical compound, a low cost electro-luminescent device including a luminous layer that contains the chemical compound, and a display apparatus that includes a plurality of the electro-luminescent devices, in which the above disadvantage are eliminated.

One of the above objects of the present invention is achieved by a chemical compound containing a main chain that contains at least one substituted or non-substituted 2,5-thiophenediyl group and at least one substituted or non-substituted 9-carbazolyl group that bonds to at least one of two terminals of the main chain.

According to the present invention described above, there can be provided a chemical compound capable of emitting visible light and having electrical conductivity.

Preferably, the number of the substituted or non-substituted 9-carbazolyl groups is two and each of the two substituted or non-substituted 9-carbazolyl groups separately bonds to one of the two terminals of the main chain.

According to the present invention described above, there can be provided a chemical compound capable of emitting visible light and having high electrical conductivity and high thermal resistance, which is easy to synthesize.

More preferably, the substituted or non-substituted 2,5-thiophenediyl group is a non-substituted 2,5-thiophenediyl group, the substituted or non-substituted 9-carbazolyl group is a non-substituted 9-carbazolyl group, and the number of the non-substituted 2,5-thiophenediyl groups is two through six. Specifically, in this case, the chemical compound is one of 2,5'-di(9-carbazolyl)-5,2'-bithiophene, 2,5''-di(9-carbazolyl)-5,2':5',2''-terthiophene, 2,5'''-di(9-carbazolyl)-5,2':5',2'':5'',2'''-quaterthiophene, 2,5''''-di(9-carbazolyl)-5,2':5',2'':5'',2''':5''',2''''-quinquethiophene, and 2,5'''''-di(9-carbazolyl)-5,2':5',2'':5'',2''':5''',2'''':5'''',2'''''-sexithiophene.

According to the present invention described above, there can be provided a group of chemical compounds capable of emitting visible light at various wavelengths that cover a wide range of the spectral region of visible light.

Also, one of the above objects of the present invention is achieved by a luminescent material that contains the chemical compound described above.

According to the present invention described above, there can be provided a luminescent material that contains a chemical compound capable of emitting visible light and having electrical conductivity.

Also, one of the above objects of the present invention is achieved by an electro-luminescent device that includes a substrate, an anode, a cathode, and a luminous layer between the anode and the cathode, in which the anode, the luminous layer, and the cathode are laminated on the substrate, wherein the luminous layer contains the chemical compound described above.

According to the present invention described above, there can be provided a low cost electro-luminescent device including a luminous layer that contains a chemical compound capable of emitting visible light and having electrical conductivity.

Also, one of the above objects of the present invention is achieved by a display apparatus that includes a plurality of the electro-luminescent devices described above.

According to the present invention described above, there can be provided a display apparatus that includes a plurality of low cost electro-luminescent devices, which electro-luminescent device includes a luminous layer that contains a chemical compound capable of emitting visible light and having electrical conductivity.

BRIEF DESCRIPTION OF THE DRAWINGS

Other objects, features and advantages of the present invention will become more apparent from the following detailed description when read in conjunction with the accompanying drawings, in which.

DETAILED DESCRIPTION OF THE PREFERRED EMBODIMENTS

Figure 1:
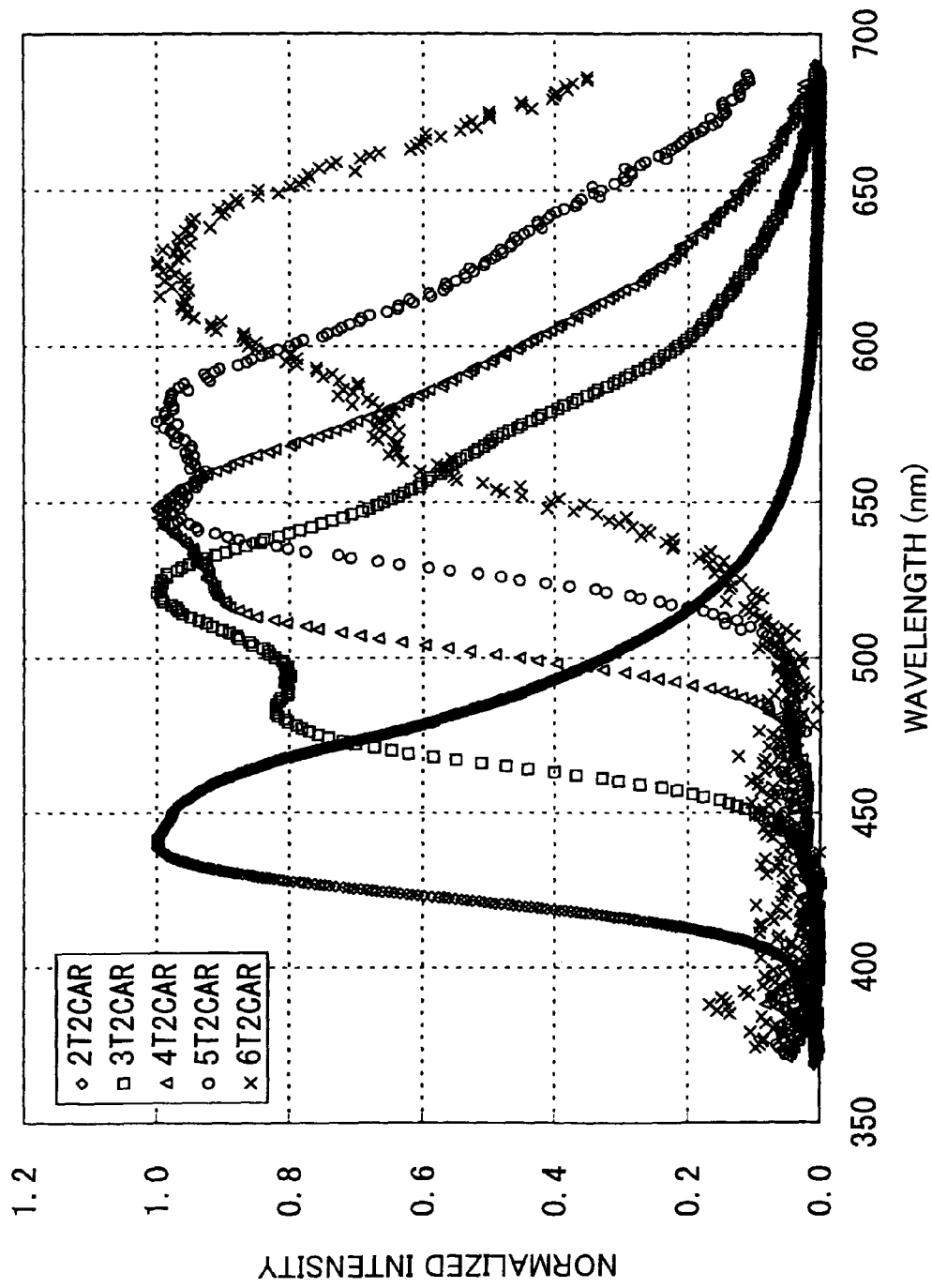
FIG. 1 is a graph showing emission spectra measured with respect to some chemical compounds according the present invention.

A description is hereinafter given of embodiments of the present invention, by referring to the drawings.

First, the structure of a chemical compound according to the present invention is illustrated below. The chemical compound according to the present invention is a chemical compound containing a main chain that contains at least one substituted or non-substituted 2,5-thiophenediyl group represented by

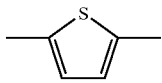

(when a plurality of substituted or non-substituted 2,5-thiophenediyl groups are contained in the chemical compound, the substituted or non-substituted 2,5-thiophenediyl groups couple to each other), and one or two substituted or non-substituted 9-carbazolyl groups represented by

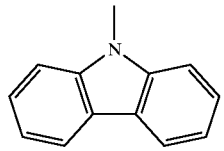

that bond to either or both of the two terminals of the main chain. Herein, when one 9-carbazolyl group bonds to one of the two terminals of the main chain, an arbitrary substituent other than 9-carbazolyl group bonds to the other terminal of the main chain.

The number of the substituted or non-substituted 2,5-thiophenediyl groups contained in the main chain of the chemical compound according to the present invention is preferably 1 through 10.

The 2,5-thiophenediyl group may have one or two substituents. Also, when the 2,5-thiophenediyl group has one or two substituents, the position(s) of the substituent(s) is/are 3-position or/and 4-position of the 2,5-thiophenediyl group.

In respect to the kind of the substituent for the 2,5-thiophenediyl group, any kind of substituent for substituting one or two hydrogen atoms at 3-position and/or 4-position of the 2,5-thiophenediyl group can be employed. The substituent is preferably a linear or branched alkyl group that contains 1 through 20 carbon atom(s), such as methyl, ethyl, n-propyl, isopropyl, n-butyl, isobutyl, sec-butyl, tert-butyl, n-pentyl, n-hexyl, n-heptyl, n-octyl, n-nonyl, and n-decyl, a cycloalkyl group that contains 3 through 10 carbon atoms, such as cyclopropyl, cyclobutyl, cyclopentyl, and cyclohexyl, a linear or branched alkenyl group that contains 2 through 20 carbon atoms, such as vinyl, allyl, 1-butenyl, 2-butenyl, and 3-pentenyl, a cycloalkenyl group that contains 3 through 10 carbon atoms, such as cyclopropenyl, cyclobutenyl, cyclopentenyl, and cyclohexenyl, a linear or branched alkynyl group that contains 2 through 20 carbon atoms, such as ethynyl, propargyl, and 3-pentynyl, a dienyl group that contains 4 through 20 carbon atoms, such as 1,3-butadienyl, a linear or branched alkoxy group that contains 1 through 20 carbon atom(s), such as methoxy, ethoxy, propoxy, and butoxy, a hydroxyl group, a carboxyl group, an aldehyde group, a linear or branched acyl group that contains 2 through 20 carbon atoms, such as acetyl, propionyl, butyryl, isobutyryl, pentanoyl, and hexanoyl, an amino group, a cyano group, a sulfonic group, a halogen group such as fluoro, chloro, bromo, and iodo, a monocyclic or condensed polycyclic aryl group that contains 5 through 14 carbon atoms, such as phenyl, 1,3-cyclopentadiene-1-yl, 2-indenyl, 1-naphtyl, 2-naphtyl, 2-anthryl, 2-phenanthryl, and 4-biphenylyl, and a heterocyclic group that contains at least one carbon atom and at least one hetero atom such as a nitrogen atom, an oxygen atom, and a sulfur atom, the total number of the carbon atom(s) and the hetero atom(s) being 5 through 14, such as pyrrolyl, imidazolyl, pyrazolyl, pyridyl, pyrazinyl, pyrimidinyl, furyl, thienyl, thiazolyl, isothiazolyl, oxazolyl, isoxazolyl, quinolyl, indolyl, carbazolyl, and acridinyl.

When the substituent is an acyclic group, the number of carbon atoms contained in the substituent is preferably equal to or more than 4.

The substituent for the 2,5-thiophenediyl group may be a ring group that shares a bond between carbon atoms at 3-position and 4-position of the 2,5-thiophenediyl group. Such a ring group is preferably a divalent group of a cycloalkane that contains 3 through 10 carbon atoms such as cyclopropane, cyclobutane, cyclopentane, and cyclohexane, a divalent group of a monocyclic or condensed polycyclic aromatic hydrocarbon that contains 5 through 14 carbon atoms such as benzene, cyclopentadiene, indene, naphthalene, anthracene, phenanthrene, and biphenyl, and a divalent group of a heterocyclic compound that contains at least one carbon atom and at least one hetero atom such as a nitrogen atom, an oxygen atom, and a sulfur atom, the total number of the carbon atom(s) and the hetero atom(s) being 5 through 14, such as pyrrole, imidazole, pyrazole, pyridine, pyrazine, pyrimidine, furan, thiophene, thiazole, isothiazole, oxazole, isoxazole, quinoline, indole, carbazole, and acridine. Herein, those divalent groups have two free valences at two adjacent atoms in the ring.

Also, when the chemical compound according to the present invention contains a plurality of the 2,5-thiophenediyl groups, the presence or absence, the position, and the kind of a substituent are determined independently among the 2,5-thiophenediyl groups. It goes without saying that identical substituents may bond to all the 2,5-thiophenediyl groups at the same positions. For example, both hydrogen atoms at 3-position and 4-position in all the 2,5-thiophenediyl groups may be substituted with the identical substituents. Also, either of hydrogen atoms at 3-position and 4-position in all the 2,5-thiophenediyl groups may be substituted with the identical substituents.

The 9-carbazolyl group(s) bonding to either or both of two terminals of the main chain in the chemical compound according to the present invention may also have a substituent. When the 9-carbazolyl group has a substituent, the substituent can bond to any of 1- through 8-positions of the 9-carbazolyl group, and a plurality of substituents may bond to a plurality of the positions of the 9-carbazolyl group.

In respect to the kind of the substituent for 9-carbazolyl group, any kind of substituent for substituting at least one hydrogen atom of the 9-carbazolyl group can be employed. The substituent is preferably a linear or branched alkyl group that contains 1 through 20 carbon atom(s), such as methyl, ethyl, n-propyl, isopropyl, n-butyl, isobutyl, sec-butyl, tert-butyl, n-pentyl, n-hexyl, n-heptyl, n-octyl, n-nonyl, and n-decyl, a cycloalkyl group that contains 3 through 10 carbon atoms, such as cyclopropyl, cyclobutyl, cyclopentyl, and cyclohexyl, a linear or branched alkenyl group that contains 2 through 20 carbon atoms, such as vinyl, allyl, 1-butenyl, 2-butenyl, and 3-pentenyl, a cycloalkenyl group that contains 3 through 10 carbon atoms, such as cyclopropenyl, cyclobutenyl, cyclopentenyl, and cyclohexenyl, a linear or branched alkynyl group that contains 2 through 20 carbon atoms, such as ethynyl, propargyl, and 3-pentynyl, a dienyl group that contains 4 through 20 carbon atoms, such as 1,3-butadienyl, a linear or branched alkoxy group that contains 1 through 20 carbon atom(s), such as methoxy, ethoxy, propoxy, and butoxy, a hydroxyl group, a carboxyl group, an aldehyde group, a linear or branched acyl group that contains 2 through 20 carbon atoms, such as acetyl, propionyl, butyryl, isobutyryl, pentanoyl, and hexanoyl, an amino group, a cyano group, a sulfonic group, a halogen group such as fluoro, chloro, bromo, and iodo, a monocyclic or condensed polycyclic aryl group that contains 5 through 14 carbon atoms, such as phenyl, 1,3-cyclopentadiene-1-yl, 2-indenyl, 1-naphtyl, 2-naphtyl, 2-anthryl, 2-phenanthryl, and 4-biphenylyl, and a heterocyclic group that contains at least one carbon atom and at least one hetero atom such as a nitrogen atom, an oxygen atom, and a sulfur atom, the total number of the carbon atom(s) and the hetero atom(s) being 5 through 14, such as pyrrolyl, imidazolyl, pyrazolyl, pyridyl, pyrazinyl, pyrimidinyl, furyl, thienyl, thiazolyl, isothiazolyl, oxazolyl, isoxazolyl, quinolyl, indolyl, carbazolyl, and acridinyl.

When the substituent is an acyclic group, the number of carbon atoms contained in the substituent is preferably equal to or more than 4.

The substituent for the 9-carbazolyl group may be a ring group that shares a bond between adjacent carbon atoms of the 9-carbazolyl group. Such a ring group is preferably a divalent group of a cycloalkane that contains 3 through 10 carbon atoms such as cyclopropane, cyclobutane, cyclopentane, and cyclohexane, a divalent group of a monocyclic or condensed polycyclic aromatic hydrocarbon that contains 5 through 14 carbon atoms such as benzene, cyclopentadiene, indene, naphthalene, anthracene, phenanthrene, and biphenyl, and a divalent group of a heterocyclic compound that contains at least one carbon atom and at least one hetero atom such as a nitrogen atom, an oxygen atom, and a sulfur atom, the total number of the carbon atom(s) and the hetero atom(s) being 5 through 14, such as pyrrole, imidazole, pyrazole, pyridine, pyrazine, pyrimidine, furan, thiophene, thiazole, isothiazole, oxazole, isoxazole, quinoline, indole, carbazole, and acridine. Herein, those divalent groups have two free valences at two adjacent atoms in the ring.

Also, when two 9-carbazolyl groups bond to both of the two terminals of the main chain in the chemical compound according to the present invention, the presence or absence, the position, and the kind of a substituent are determined independently between both 9-carbazolyl groups. When two substituted or non-substituted 9-carbazolyl groups bond to both of the two terminals of the main chain of the chemical compound according to the present invention, it is preferable that the two substituted or non-substituted 9-carbazolyl groups not be identical to each other.

When one 9-carbazolyl group bonds to either of the two terminals of the main chain in the chemical compound according to the present invention, an arbitrary substituent can bond to the other terminal of the main chain. The substituent is preferably a hydrogen atom, a linear or branched alkyl group that contains 1 through 20 carbon atom(s), such as methyl, ethyl, n-propyl, isopropyl, n-butyl, isobutyl, sec-butyl, tert-butyl, n-pentyl, n-hexyl, n-heptyl, n-octyl, n-nonyl, and n-decyl, a cycloalkyl group that contains 3 through 10 carbon atoms, such as cyclopropyl, cyclobutyl, cyclopentyl, and cyclohexyl, a linear or branched alkenyl group that contains 2 through 20 carbon atoms, such as vinyl, allyl, 1-butenyl, 2-butenyl, and 3-pentenyl, a cycloalkenyl group that contains 3 through 10 carbon atoms, such as cyclopropenyl, cyclobutenyl, cyclopentenyl, and cyclohexenyl, a linear or branched alkynyl group that contains 2 through 20 carbon atoms, such as ethynyl, propargyl, and 3-pentynyl, a dienyl group that contains 4 through 20 carbon atoms, such as 1,3-butadienyl, a linear or branched alkoxy group that contains 1 through 20 carbon atom(s), such as methoxy, ethoxy, propoxy, and butoxy, a hydroxyl group, a carboxyl group, an aldehyde group, a linear or branched acyl group that contains 2 through 20 carbon atoms, such as acetyl, propionyl, butyryl, isobutyryl, pentanoyl, and hexanoyl, an amino group, a cyano group, a sulfonic group, a halogen group such as fluoro, chloro, bromo, and iodo, a monocyclic or condensed polycyclic aryl group that contains 5 through 14 carbon atoms, such as phenyl, 1,3-cyclopentadiene-1-yl, 2-indenyl, 1-naphtyl, 2-naphtyl, 2-anthryl, 2-phenanthryl, and 4-biphenylyl, and a heterocyclic group that contains at least one carbon atom and at least one hetero atom such as a nitrogen atom, an oxygen atom, and a sulfur atom, the total number of the carbon atom(s) and the hetero atom(s) being 5 through 14, such as pyrrolyl, imidazolyl, pyrazolyl, pyridyl, pyrazinyl, pyrimidinyl, furyl, thienyl, thiazolyl, isothiazolyl, oxazolyl, isoxazolyl, quinolyl, indolyl, carbazolyl, and acridinyl.

However, it is preferable that two 9-carbazolyl groups bond to both of the two terminals of the main chain in the chemical compound according to the present invention. When two 9-carbazolyl groups bond to both terminals of the main chain of the chemical compound according to the present invention, the chemical compound is represented by the general formula (1):

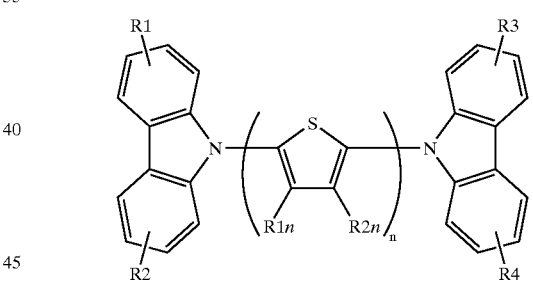

Herein, n is the number of the 2,5-thiophenediyl group(s) and an integer of 1 through 10. Also, each of R1n and R2n (wherein n=1 through 10) is a hydrogen atom or a substituent for the 2,5-thiophenediyl group described above (R1n and R2n may form a ring group), and each of R1, R2, R3, and R4 is a hydrogen atom or a substituent for the 9-carbazolyl group described above.

Next, the property of the chemical compound according to the present invention will be explained below. The chemical compound according to the present invention emits visible light with a wavelength in a specific spectral region using proper excitation means and has electric conductivity.

The wavelength of the visible light emitted from the chemical compound according to the present invention can be changed by changing the number of the 2,5-thiophenediyl group(s). Additionally, the wavelength of the visible light emitted from the chemical compound according to the present invention is changed dependent on the presence or absence, the position, and the kind of the substituent for the 2,5-thiophenediyl group. That is, the fewer the number of the 2,5-thiophenediyl groups is, the shorter the wavelength of the emitted visible light is. On the other hand, the more the number of the 2,5-thiophenediyl groups is, the longer the wavelength of the emitted visible light is. When the 2,5-thiophenediyl group number is 1, visible light with approximately purple color is emitted. Additionally, as two 9-carbazolyl groups bond to both terminals of the main chain in the chemical compound according to the present invention, the wavelength of the emission is shifted to be longer, compared to the case of the 9-carbazolyl group bonding to either of the two terminals of the main chain.

Also, the chemical compound according to the present invention has high electric conductivity since the 9-carbazolyl group(s) bond(s) to either or both of the two terminals of the main chain in the chemical compound. The main chain of the chemical compound that contains 2,5-thiophenediyl group(s) having a hetero atom S contributes to the electric conductivity of the chemical compound. In addition, it is believed that one or two 9-carbazolyl group(s) containing an N atom contribute(s) to the movement of carriers (that is, holes or electrons) caused by the hopping of the carriers between the molecules of the chemical compound according to the present invention. As the result, the chemical compound according to the present invention results in having high electrical conductivity.

Additionally, the chemical compound according to the present invention is not a polymer since the number of the 2,5-thiophenediyl group(s) is 1 through 10. Accordingly, the molecular weight of the chemical compound is not so large, and a film can uniformly be formed from the chemical compound according to the present invention by using a well-known vacuum deposition method.

As one or two 9-carbazolyl group(s) bond(s) to either or both of the two terminals of the main chain in the chemical compound according to the present invention, the chemical compound can emit visible light. However, when two 9-carbazolyl groups bond to both of the two terminals of the main chain in the chemical compound according to the present invention, the molecular structure of the chemical compound is more symmetric as indicated in the general formula (1), so that the chemical compound is easily synthesized, compared with a chemical compound according to the present invention that contains one 9-carbazolyl group bonding to either of the two terminals of the main chain. Also, a chemical compound according to the present invention that contains two 9-carbazolyl groups bonding to both of the two terminals of the main chain has electrical conductivity higher than that of a chemical compound according to the present invention that contains one 9-carbazolyl group bonding to either of the two terminals of the main chain. Furthermore, the chemical compound according to the present invention that contains two 9-carbazolyl groups bonding to both of the two terminals of the main chain has a comparatively large molecular weight so as to have a high melting point. Accordingly, a chemical compound having high thermal resistance can be obtained.

As described above, the number of the 2,5-thiophenediyl group(s) is preferably 1 through 10 in the present invention. If the number of the 2,5-thiophenediyl groups is greater than 10, the chemical compound according to the present invention does not emit visible light but infrared light, since the chemical compound has a large conjugate system. However, the wavelength of the emission depends on the presence or absence, the position, and the kind of a substituent for the 2,5-thiophenediyl group(s). In addition, as the number of the 2,5-thiophenediyl groups is greater than 10, the molecule of the chemical compound becomes large. Accordingly, the number of the molecular vibration modes of the chemical compound greatly increases, so that the loss of the molecular vibration energy also increases and the efficiency of the emission much decreases. On the other hand, the fewer the number of the 2,5-thiophenediyl groups is, the easier the chemical compound can be synthesized.

In the chemical compound according to the present invention, the wavelength of the emitted visible light can be shifted as at least one proper substituent to the 2,5-thiophenediyl group(s) is introduced. Additionally, the electrical conductivity of the chemical compound can be improved by introducing at least one proper substituent to the 9-catbazolyl group(s). Particularly, the substituent for improving the electrical conductivity is preferably an alkyl group, of which the number of carbon atoms is equal to or more than 4. Also, when two substituted or non-substituted 9-carbazolyl groups bond to both of the two terminals of the main chain in the chemical compound according to the present invention, it is preferable that the two substituted or non-substituted 9-carbazolyl groups be not identical. When the two substituted or non-substituted 9-carbazolyl groups are not identical, the molecular structure of the chemical compound according to the present invention is asymmetric, so that the molecules of the chemical compound are not regularly arranged at a solid state and the chemical compound is difficult to crystallize. Thus, the solid of the chemical compound is prevented from becoming clouded and keeps high transparency thereof, by suppression of the crystallization of the chemical compound.

Next, a method for synthesizing the chemical compound according to the present invention will be explained below. The method for synthesizing the chemical compound according to the present invention generally includes step 1 of coupling a plurality of substituted or non-substituted 2,5-thiophenediyl groups to form a main chain of the chemical compound according to the present invention and step 2 of coupling one or two substituted or non-substituted 9-carbazolyl groups to either or both of the two terminals of the main chain that contains the substituted or non-substituted 2,5-thiophenediyl group(s). Herein, when a chemical compound according to the present invention that contains one substituted or non-substituted 2,5-thiophenediyl group is synthesized, or when a chemical compound that contains a plurality of substituted or non-substituted 2,5-thiophenediyl groups coupled to each other is previously obtained, the above-mentioned step 1 is omitted.

In order to synthesize a chemical compound according to the present invention that contains 2,5-thiophenediyl group(s) having a substituent thereof, a substituted thiophene provided by previously substituting one or two hydrogen atoms at 3-position and/or 4-position of thiophene with a desired substituent is obtained, or a substituted thiophene is synthesized from thiophene using a proper method. Also, in order to synthesize a chemical compound according to the present invention that contains 9-carbazolyl group(s) having a substituent thereof, a substituted carbazole provided by previously substituting at least one hydrogen atom at a desired position of carbazole except at the position of N atom with a desired substituent is obtained, or a substituted carbazole is synthesized from carbazole using a proper method. Additionally, in respect to the synthesis of the substituted carbazole, it is easy to introduce at least one substituent to 4-position and/or 7-position of the carbazole, at which the substitution reactivity is high. In order to synthesize a chemical compound according to the present invention that contains non-substituted 2,5-thiophenediyl group and/or non-substituted 9-carbazolyl group, thiophene and/or carbazole are/is used as (a) starting material(s) of the synthesis, respectively.

There are provided two methods for the synthesis in step 1. First, a method of synthesizing a chemical compound according to the present invention that contains comparatively fewer (equal to or less than 5) substituted or non-substituted 2,5-thiophenediyl group(s) will be explained below. One or two hydrogen atoms at highly reactive 2-position and/or 5-position of the substituted (at 3-position and/or 4-position) or non-substituted thiophene are substituted with one or two bromine atoms at ordinary or higher temperature using N-brormosuccinimide (NBS), etc. The brominated product is referred to as TBr below. Then, a chemical compound of which one or two hydrogen atoms at 2-position and/or 5-position of the substituted or non-substituted thiophene are substituted with one or two bromine atoms is separately obtained or synthesized according to the above-mentioned method. Then, the obtained or synthesized product is reacted with magnesium to prepare a Grignard reagent, wherein the Grignard reagent is a thienylmagnesium bromide. The Grignard reagent is referred to as TMgBr. Then, the TBr is reacted with the TMgBr under the presence of a proper catalyst, so that one or two bromine atoms at 2-position and/or 5-position of TBr are substituted with one or two substituted or non-substituted thienyl groups in the TMgBr. Thus, from a TBr provided by substituting both hydrogen atoms at both 2-position and 5-position of the substituted or non-substituted thiophene with Br, synthesized is a chemical compound that contains three substituted or non-substituted thiophenes coupled to each other at the 2-position and the 5-position. On the other hand, from a TBr provided by substituting one hydrogen atom at either 2-position or 5-position of the substituted or non-substituted thiophene with Br, synthesized is a chemical compound that contains two substituted or non-substituted thiophenes coupled to each other at the 2-position or the 5-position. A chemical compound that contains four or five substituted or non-substituted thiophenes coupled to each other at the 2-positions and the 5-positions can be synthesized by repeating the above-mentioned bromination and the reaction with the Grignard reagent.

Second, a method of synthesizing a chemical compound according to the present invention that contains comparatively more (6 through 10) substituted or non-substituted 2,5-thiophenediyl groups will be explained below. In this case, a plurality of thiophenes can be coupled to each other at the highly reactive 2- and 5-positions under the presence of a catalyst such as iron chloride (II). Thus, a chemical compound that contains comparatively more substituted or non-substituted thiophenes coupled to each other at the 2-positions and the 5-positions can be synthesized. The chemical compound is referred to as nT below for the purpose of simplicity.

In step 2, first, in the product obtained by using the above-mentioned method that contains one or more substituted or non-substituted thiophenes or the nT, either or both of two hydrogen atoms at 2- and 5-positions being terminals of one or more coupled 2,5-thiophenediyl groups are substituted with one or two bromine atoms by using NBS, etc., as similar to the above-mentioned bromination. The brominated product is reacted with one or two substituted (with respect to at least one hydrogen atom bonding to a carbon atom) or non-substituted carbazoles at high temperature under the presence of a catalyst such as copper, etc. When both of two hydrogen atoms at 2- and 5-positions being terminals of one or more coupled 2,5-thiophenediyl groups are substituted with two bromine atoms, a chemical compound that contains two substituted or non-substituted 9-carbazolyl groups bonding to both terminals of the main chain of the chemical compound is produced. On the other hand, when either of two hydrogen atoms at 2- and 5-positions being terminals of one or more coupled 2,5-thiophenediyl groups is substituted with one bromine atom, a chemical compound that contains one substituted or non-substituted 9-carbazolyl group bonding to either of the two terminals of the main chain of the chemical compound is produced.

Next, the application of the chemical compound according to the present invention will be explained below.

The chemical compound according to the present invention is employed in various luminescent materials since visible light with a wavelength in a specific spectral region can be emitted using proper excitation means. For example, the chemical compound according to the present invention is used in paint that emits visible light due to irradiation of ultraviolet rays, etc.

Also, the chemical compound according to the present invention is used as various electrically conducive materials since the chemical compound has electric conductivity. Additionally, the chemical compound according to the present invention is preferably used as a material for the luminous layer in the EL device, since the chemical compound emits visible light with a wavelength in a specific spectral region and has electric conductivity. That is, an EL device that includes a luminous layer containing the chemical compound according to the present invention can be provided. Also, an EL display apparatus in which such EL device(s) is/are arranged on a substrate thereof can be provided. The EL device that includes a luminous layer containing the chemical compound according to the present invention and the EL display apparatus can be produced by a conventional production method. Additionally, when only a part of the wavelength region of the visible light emitted from the chemical compound according to the present invention is utilized, visible light with a wavelength in an unnecessary spectral region may be cut off using a proper narrow band filter.

Also, a group of the chemical compounds according to the present invention and luminescent materials that contain the chemical compounds can be provided, in which the wavelength of visible light emitted from one of the chemical compounds in the group is different from that from another chemical compound in the group. The wavelength of visible light emitted from the chemical compound in the group can be adjusted by changing the number of substituted or non-substituted 2,5-thiophenediyl group(s) contained in the main chain of the chemical compound. Accordingly, the chemical compounds in the group can emit visible light with a wavelength in various spectral regions such as the red light region, green light region, and blue light region, respectively. Also, the chemical compounds in the group have similar substituted or non-substituted 2,5-thiophenediyl groups in the main chains thereof and thus similar values for a parameter in respect to a physical property thereof such as the ionic potential, etc.

In producing one or more electronic devices, such as a plurality of EL devices, which include a luminous layer containing one of the chemical compounds according to the present invention, and an EL display apparatus that includes a plurality of the EL devices, since the chemical compounds according to the present invention in the EL devices have similar structures to each other, the service lives of the EL devices that emit the luminous colors different from each other are approximately the same. In addition, a plurality of the EL devices that emit the luminous colors different from each other are formed in the same lamination structures. Thus, the chemical compounds according to the present invention having similar molecular structures and emitting visible light with wavelengths in a spectral region different from each other are used in the EL devices, so as to provide low cost EL devices and thus a low cost EL display apparatus.

EXAMPLES

First, the synthesis method and the identification of 2,5""-di(9-carbazolyl)-5,2':5',2":5",2'":5'",2""-quinquethiophene is illustrated, which is a chemical compound employed as an example according to the present invention. The chemical compound was synthesized using the following 4 steps (A) through (D).

(A) The Synthesis of 2,5"-dibromo-5,2':5',2"-terthiophene 5.114 g (20.5 mmol) of 5,2':5',2"-terthiophene was dissolved into 100 ml of dried N,N'-dimethylformamide (DMF), and then the obtained solution was thrown into a four-neck separable flask, of which the inside air had been fully replaced with Ar gas and subsequently stirred. A solution prepared by dissolving 7.712 g (43.3 mmol) of N-bromosuccinimide (NBS) into 50 ml of dried DMF was dropped into the previously prepared 5,2':5',2"-terthiophene for 20 minutes and the obtained mixture was stirred for reaction of them for 3 hours. During the reaction caused by the stirring, a large amount of yellow precipitate was yielded. After the end of the reaction, the precipitate was washed with a sufficient amount of water and a yellow specified substance was obtained through filtration. After the specified substance was dried in a vacuum, the specified substance was recrystallized from toluene and n-hexane so as to obtain yellow needle crystals.

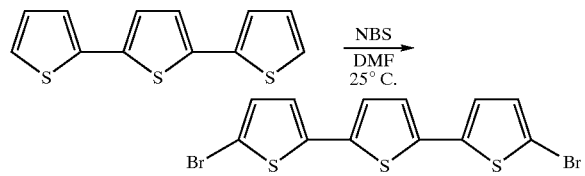

The melting point of the obtained crystals was measured by using the different thermal analysis and the melting point was 156° C., which was obtained by observing a single peak with respect to the temperature difference between the obtained yellow crystal and a reference material. The measured value of the melting point was compared with the value range 155° C. through 157° C. disclosed in the document "PREPARATION OF α-QUARTER-, α-SEXI-, AND α-OCTITHIOPHENES-HETEROCYCLES, VOL. 26, NO. 7, 1987", and the obtained yellow crystal was confirmed to be 2,5"-dibromo-5,2':5',2"-terthiophene (referred to as 3T2Br below for simplicity) being the specified substance in step (A).

(B) The Synthesis of 5,2':5',2":5",2'":5'",2""-quinquethiophene 0.724 g (29.8 mmol) of magnesium and 15 ml of dried diethylether were thrown into a three-necked flask. After air inside the flask was fully replaced with Ar gas, while the solution in the flask was stirred using a stirrer, a solution prepared by dissolving 4.859 g (29.8 mmol) of 2-bromothiophene into 10 ml of diethylether was dropped into the solution in the flask through a dropping funnel for 20 minutes. While the generation of a Grignard reagent was started, the diethylether started to boil, and then the color of the solution changed to be brown.

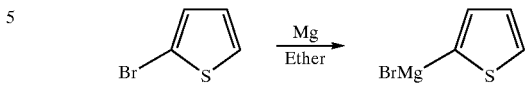

6.052 g (14.9 mmol) of 3T2Br synthesized in step (A) and 60 mg of dichloro[1,3-propanediylbis(diphenylphosphine)-κ²P]nickel (II) (referred to as $NiCl_2(PPP)$, below) were dissolved into 250 ml of diethylether and refluxed and stirred in a separable flask, of which the inside air had been fully replaced with Ar gas. At this time, the 3T2Br was not completely dissolved. Then, a solution containing the Grignard reagent obtained by a generation reaction of the Grignard reagent for approximately 1 hour was dropped into the separable flask for 20 minutes using a dropping funnel. During the dropping of the Grignard reagent, the color of the solution changed to be orange. After the Grignard reaction for 3 hours, the solution was subjected to filtration and an obtained precipitate was washed with diethylether, heated n-hexane, heated acetone, and water. Subsequently, the precipitate was recrystallized from toluene so as to obtain orange powder.

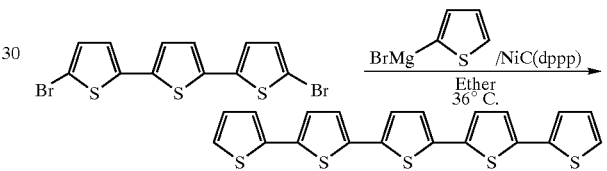

The melting point of the obtained powder crystals was measured by using the different thermal analysis and the melting point was 256° C., which was obtained by observing a single peak with respect to the temperature difference between the obtained powder and a reference material. The measured value of the melting point was compared with the value range 256° C. through 257° C. disclosed in the document "THE SYNTHESIS OF ALPHA-THIOPHENE OLIGOMERS VIA ORGANOBORANES TETRAHEDRON LETTERS, VOL. 24, NO. 38, PP4043–4046, 1983", and the obtained powder was confirmed to be 5,2':5',2":5",2'":5'",2""-quinquethiophene (referred to as 5T below for simplicity) being the specified substance in step (B).

(C) The Synthesis of 2,5""-dibromo-5,2':5',2":5",2'":5'",2""-quinquethiophene 1.995 g (4.83 mmol) of 5T synthesized in step (B) and 300 ml of dried DMF were thrown into a four-necked separable flask, of which the inside air had been fully replaced with Ar gas. The temperature of the 5T solution was maintained at 90° C. by heating while the 5T solution was stirred. A solution obtained by dissolving 1.72 g (9.66 mmol) of NBS into 20 ml of dried DMF was dropped into this solution (in which the 5T was not completely dissolved) at a time, and thereby the 5T was reacted with the NBS for 1 hour and 30 minutes. At this time, the color of the solution changed immediately. After the end of the reaction, the obtained precipitate was washed with sufficient amount of water and an orange specified substance was obtained through filtration. After the specified substance was dried in a vacuum, the specified substance was washed with heated 1,2-dichloroethane.

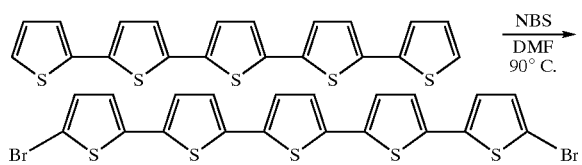

The melting point of the obtained product was measured by using the different thermal analysis and the melting point was 296° C., which was obtained by observing a single peak with respect to the temperature difference between the obtained product and a reference material. Also, as the result of the elemental analysis for the obtained product, the measured values of C:42.11, H:1.82, Br:27.96, and S:28.11 were obtained, wherein evaluated values for the product were C:42.11, H:1.77, Br:28.02, and S:28.11. Additionally, as the result of mass spectrometric analysis for the obtained product, a peak at m/e=570 corresponding to the molecular weight of 5T was measured in the mass spectrum for the product. From the above-mentioned measurement results, the obtained orange product was confirmed to be 2,5''''-dibromo-5,2':5',2'':5'',2''':5''',2''''-quinquethiophene (referred to as 5T2Br below).

(D) The Synthesis of 2,5''''-di(9-carbazolyl)-5,2':5',2'':5'', 2''':5''',2''''-quinquethiophene 1.226 g (2.15 mmol) of 5T2Br synthesized in step (C), 0.72 g (4.3 mmol) of carbazole, 0.27 g (4.3 mmol) of copper, 1.19 g (8.6 mmol) of potassium carbonate, 0.23 g of 18-crown-6, and 100 ml of o-dichlorobenzene were thrown into a four-necked separable flask, of which the inside air had been fully replaced with Ar gas. The temperature of the obtained solution was maintained at 180° C. for 96 hours, while the solution was stirred. After the end of the reaction, the obtained precipitate was washed with sufficient amount of ethyl alcohol and heated acetone. After the precipitate was filtrated, the specified substance was extracted in heated benzene. The benzene was evaporated using a rotary evaporator, so as to obtain vermilion powder. Subsequently, an impurity contained in the specified substance was eliminated using a sublimating purification method, and the pure specified substance was extracted from the residual in heated benzene.

From the result of elemental analysis for the obtained product, the measurement of C:H:N=21.58:12.43:1 was obtained, wherein the evaluation for the product is C:H: N=22:13:1. Additionally, as the result of mass spectrometric analysis for the obtained product, a peak at m/e=742 corresponding to the molecular weight of the specified substance was measured in the mass spectrum for the obtained product. Furthermore, from the measurement of 1H-NMR spectrum (400 MHz) for the obtained product in acetone, the measurement results of 7.34 (m, 12H), 7.49 (m, 6H), 7.56 (d, 4H), and 8.20 (d, 4H) were obtained, which are consistent to chemical shifts and proton number ratio expected from the chemical formula of the specified substance. From the above-mentioned measurement results, the obtained orange product was confirmed to be 2,5''''-di(9-carbazolyl)-5,2':5 ', 2'':5'',2''':5''',2''''-quinquethiophene (referred to as 5T2CAR below).

The chemical compounds that contain two, three, or four 2,5-thiophenediyl groups, synthesized in the example, that is, 2,5'-di(9-carbazolyl)-5,2'-bithiophene (as referred to as 2T2CAR below), 2,5''-di(9-carbazolyl)-5,2':5',2''-terthiophene (as referred to as 3T2CAR below), and 2,5'''-di(9-carbazolyl)-5,2':5',2'':5'',2'''-quaterthiophene (as referred to as 4T2CAR below) were also synthesized using methods similar to the above-mentioned synthesis method for the 5T2CAR.

Additionally, 2,5'''''-di(9-carbazolyl)-5,2':5',2'':5'',2''':5''', 2'''':5'''', 2'''''-sexithiophene synthesized in the example was synthesized using the following synthesis method.

First, 5,2':5',2'':5'',2''':5''',2'''':5'''',2'''''-sexithiophene (referred to as 6T below for simplicity) was synthesized. 10 g (40.26 mmol) of 5,2':5',2''-terthiophene was dissolved into 100 ml of dried benzene and the obtained solution was thrown into a four-necked separable flask fixed in a bath with an ultrasonic generator. A dispersed system obtained by dispersing 6.53 g (40.26 mmol) of iron chloride (II) into 100 ml of dried benzene was dropped into the obtained solution for 30 minutes while ultrasonic wave was applied to the solution. While nitrogen gas flowed into the flask in order to eliminate hydrogen chloride gas generated due to reaction, the reaction was promoted at room temperature for 1 hour, so as to obtain a brown product. After the reaction, the solution was thrown into a sufficient amount of water and the

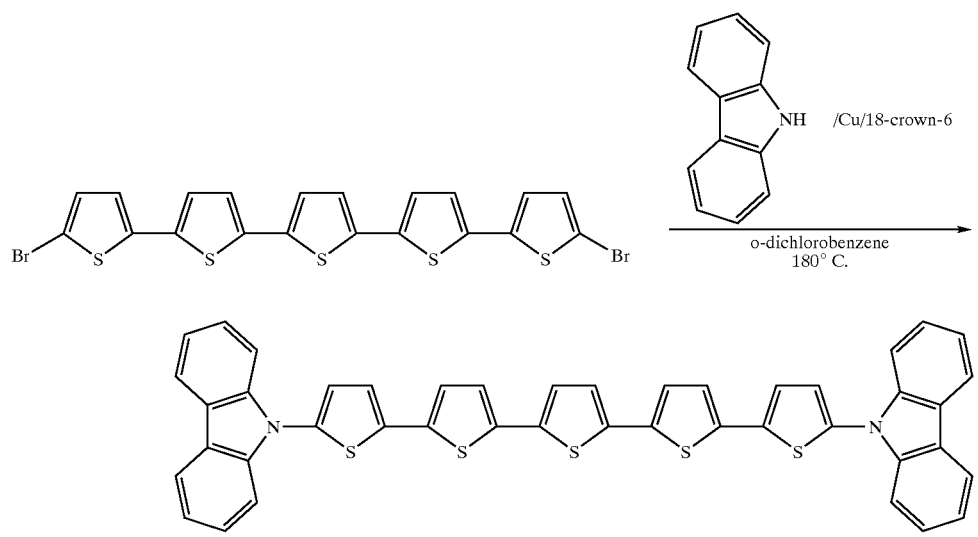

product was washed by stirring. After filtration of the product, the product was washed with acetone so as to obtain 2.95 g of henna powder. Then, the powder was purified due to sublimation so as to obtain 1 g of orange powder. The orange powder was washed with heated n-hexane.

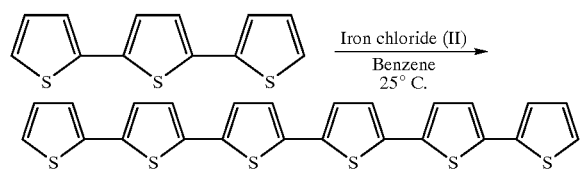

The melting point of the obtained orange powder was measured by using the different thermal analysis and the melting point was 305° C., which was obtained by observing a single peak with respect to the temperature difference between the orange powder and a reference material. The measured value of the melting point was compared with the value 304° C. disclosed in the document "PREPARATION OF α-QUARTER-, α-SEXI-, AND α-OCTITHIOPHENES-HETEROCYCLES, VOL. 26, NO. 7, 1987", and thereby the obtained powder was confirmed to be 6T being the specified substance in this step.

Then, as similar to the above-mentioned step (C), the obtained 6T was reacted with NBD dissolved into DMF at 90° C. so as to obtain 2,5''''-dibromo-5,2':5',2'':5'',2''':5''', 2'''':5'''',2'''''-sexithiophene (referred to as 6T2Br below for simplicity).

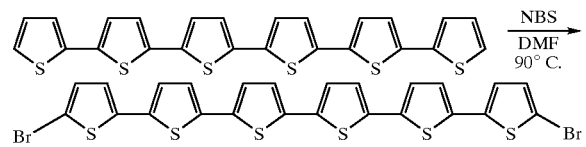

Then, as similar to the above-mentioned step (D), the 6T2Br was reacted with carbazole in o-dichlorobenzene so as to obtain 2,5''''-di(9-carbazolyl)-5,2':5',2'':5'',2°''':5''',2'''': 5''',2''''-sexithiophene (referred to as 6T2CAR below for simplicity) being the specified substance.

chemical compound normalized by the peak intensity of the light in the emission spectrum. As shown in FIG. 1, with respect to the chemical compounds synthesized in the examples, it can be understood that the greater the number of 2,5-thiophenediyl groups contained in the molecule of the chemical compound is, the longer the wavelength of the emission from the chemical compound is.

Figure 2:
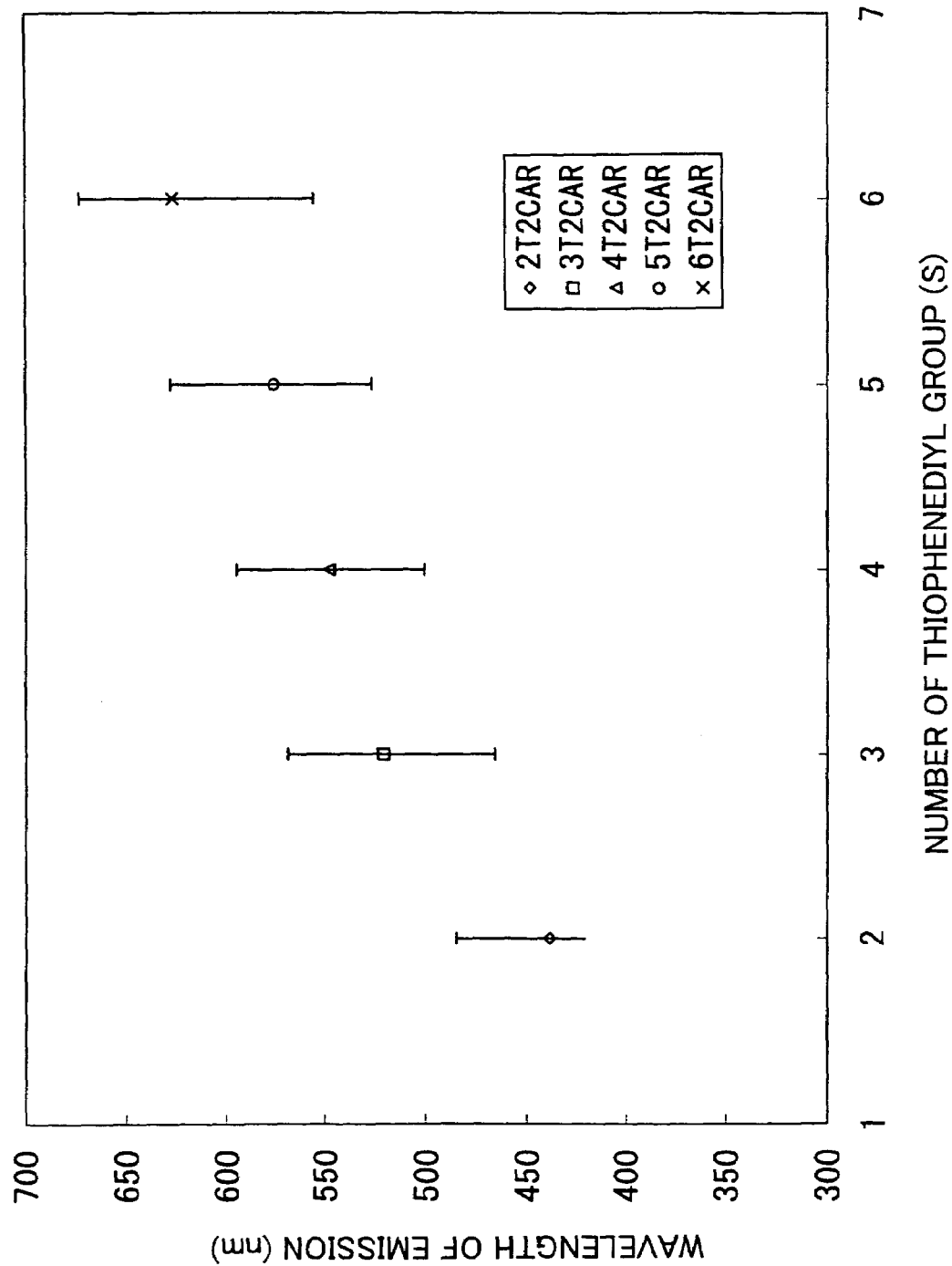
FIG. 2 is a graph showing peak wavelengths of emission spectra measured with respect to some chemical compounds according the present invention.

Now, the wavelengths of the peak intensities in the emission spectra measured for the chemical compounds synthesized in the examples are shown in FIG. 2. In FIG. 2, the horizontal axis designates the number of 2,5-thiophenediyl group(s) contained in the chemical compound and the vertical axis designates the wavelength of the emission (nm). Each point in FIG. 2 designates the wavelength at the peak intensity of the emission from each chemical compound and each bar designates a wavelength region in which the intensity of the emission from the chemical compound is equal to or more than half of the peak intensity thereof. As shown in FIG. 2, as the wavelength region in which the intensity of the emission from the chemical compound is equal to or more than half of the peak intensity thereof is regarded as a wavelength region of emission from the chemical compound, the wavelength regions of emission from the chemical compounds synthesized in the examples cover approximately the entire visible spectral region. Specifically, the wavelength regions of emission from the chemical compounds synthesized in the examples are 421 nm through 485 nm (439 nm) for the 2T2CAR, 466 nm through 569 nm (521 nm) for the 3T2CAR, 501 nm through 599 nm (548 nm) for the 4T2CAR, 527 nm through 628 nm (576 nm) for the 5T2CAR, and 556 nm through 673 nm (627 nm) for the 6T2CAR, wherein the numbers in parentheses are the wavelengths at the peak intensity of emission from each chemical compound. As referring to the wavelengths at the peak intensity, the colors of the emission are purple-blue for the 2T2CAR, green for the 3T2CAR, yellow-green for the 4T2CAR, yellow for the 5T2CAR, and red-orange for the 6T2CAR, wherein the color at a wavelength around 421 nm for the 2T2CAR is called as purple-blue and the color at a wavelength around 673 nm for the 6T2CAR is called as red (and the names of colors are as referred to in the Newly Edited Handbook of Color Science edited by The Color

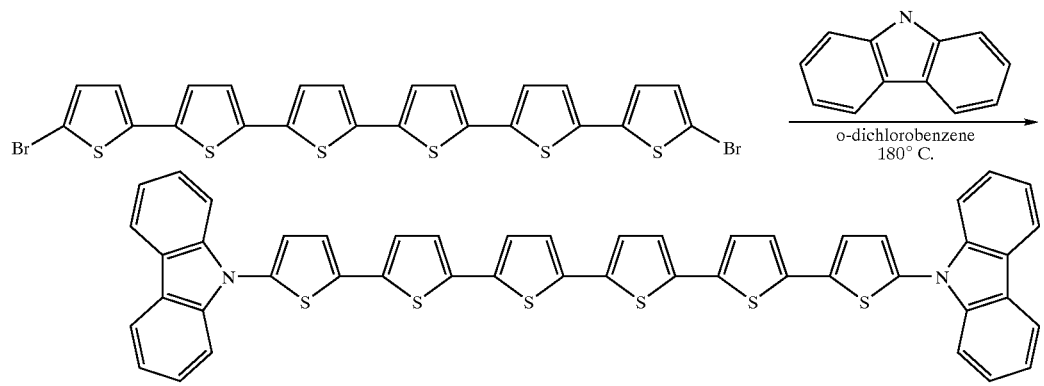

Next, the emission spectra measured for the chemical compounds synthesized in the examples, that is, 2T2CAR, 3T2CAR, 4T2CAR, 5T2CAR, and 6T2CAR are shown in FIG. 1. The horizontal axis of the graph shown in FIG. 1 designates wavelength (nm) of emitted light and the vertical axis designates the intensity of light emitted from the Science Association of Japan). As described above, emission with a desired color can be provided by appropriately selecting and using the chemical compounds synthesized in the examples.

Figure 3:
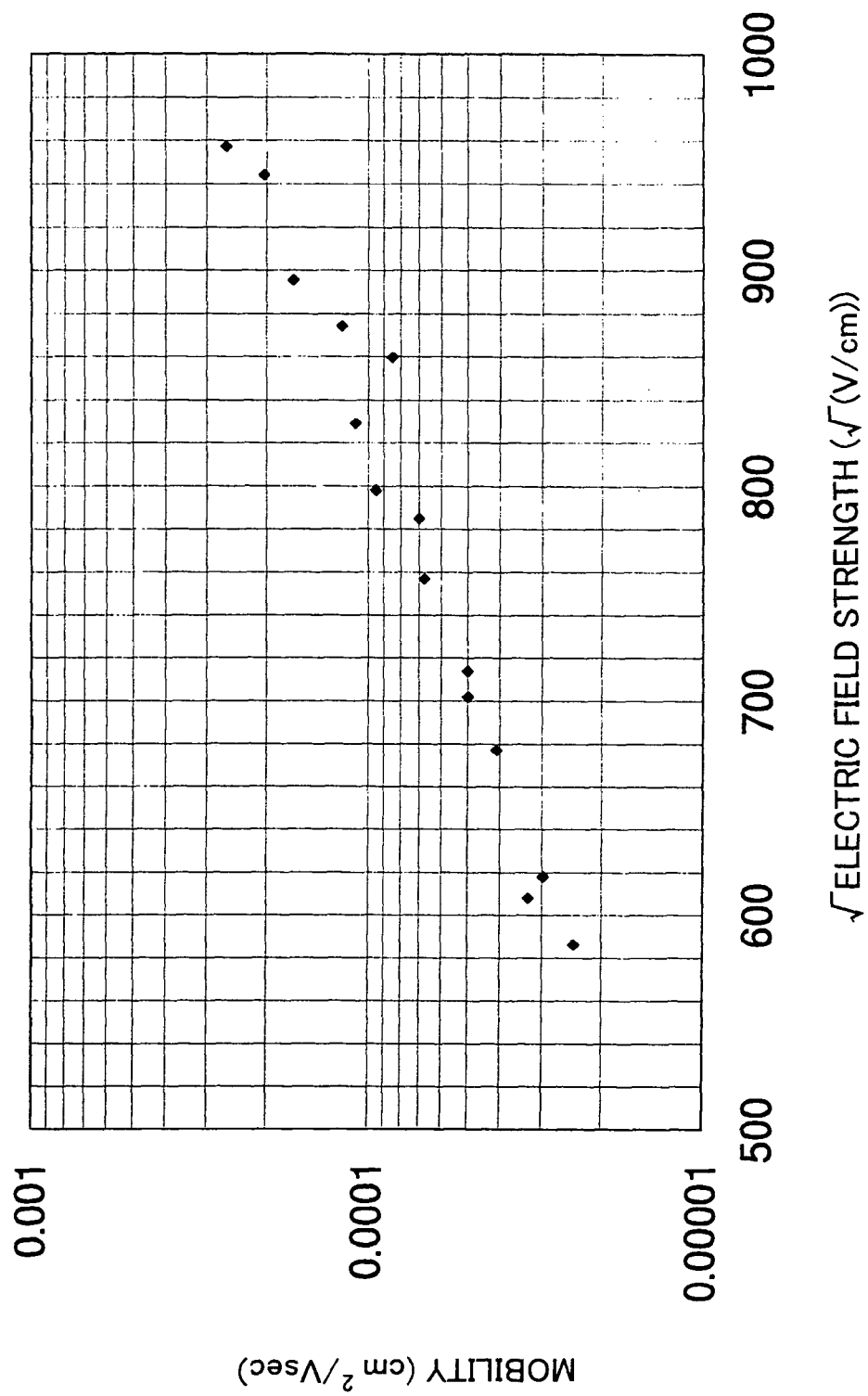
FIG. 3 is a graph showing the relationship between the mobility of holes and electrical field strength measured with respect to a chemical compound according to the present invention.

Next, the measurement result of the mobility of the holes for the 5T2CAR being one chemical compound synthesized in the examples is shown in FIG. 3. In order to confirm the electrical conductivity of the chemical compound, the mobility of the holes for the chemical compound was measured by the time-of-flight (T. O. F) method. For the measurement of the mobility a sample for measurement was manufactured by depositing an aluminum electrode as an anode on a glass substrate using an electric resistance heating-type vacuum evaporator, forming an evaporated film of the synthesized 5T2CAR on the aluminum electrode, and depositing an aluminum electrode as a cathode on the evaporated film. In FIG. 3, the horizontal axis designates the square root of an electric field strength applied between the two electrodes of the sample for measurement $((V/cm)^{1/2})$ and the vertical axis designates the mobility of the holes for the 5T2CAR in the sample for measurement $(cm^2/(Vs))$. The mobility of the holes and the electric field strength were calculated from the following formulas:

The mobility of the holes=(the thickness of the 5T2CAR film)$^2$/(the voltage applied between the two electrodes×the time-of-flight of the holes) and The electric field strength=(the voltage applied between the two electrodes)/(the thickness of the 5T2CAR film)

As shown in FIG. 3, the logarithm of the mobility of the holes was approximately in proportion to the square root of the applied electric field strength. Herein, when carriers (holes or electrons) transfer among the molecules of the chemical compound via carrier hopping, it is well known as the Gill's relation that the logarithm of the mobility of carriers is proportional to the square root of the electric field strength applied to a chemical compound. Accordingly, from the result of the measurement of the mobility of the holes due to the time-of-flight method, it was confirmed that the chemical compound 5T2CAR synthesized in one example has electric conductivity due to carrier hopping. Also, it was confirmed that the compounds synthesized in the examples other than the 5T2CAR have electric conductivity as similar to the case of the 5T2CAR.

Further, the present invention is not limited to these embodiments, but various variations and modifications may be made without departing from the scope of the present invention.

The present application is based on Japanese priority application No. 2002-174745 filed on Jun. 14, 2002, the entire contents of which are hereby incorporated by reference.

What is claimed is:

1. An electro-luminescent device comprising:
    a substrate,
    an anode,
    a cathode, and
    a luminous layer between the anode and the cathode,
    in which the anode, the luminous layer, and the cathode are laminated on the substrate,
wherein
    the luminous layer comprises a chemical compound comprising:
    (a) a main chain that consists of a substituted or non-substituted 2,5-thiophenediyl group or a plurality of substituted or non-substituted 2,5-thiophenediyl groups, said 2,5-thiophenediyl group or groups forming the main chain with two terminals, and
    (b) two substituted or non-substituted 9-carbazolyl groups, each of said 9-carbazolyl groups bonding to a respective one of the two terminals of the main chain.

2. The electro-luminescent device as claimed in claim 1, wherein
    the main chain consists of from one to ten non-substituted 2,5-thiophenediyl; groups, and
    the 9-carbazolyl groups are non-substituted 9-carbazolyl groups.

3. A display apparatus comprising:
    a plurality of electro-luminescent devices that comprise
    a substrate,
    an anode,
    a cathode, and
    a luminous layer between the anode and the cathode,
    in which the anode, the luminous layer, and the cathode are laminated on the substrate,
wherein
    the luminous layer comprises a chemical compound comprising:
    (a) a main chain that consists of a substituted or non-substituted 2,5-thiophenediyl group or a plurality of substituted or non-substituted 2,5-thiophenediyl groups, said 2,5-thiophenediyl group or groups forming the main chain with two terminals, and
    (b) two substituted or non-substituted 9-carbazolyl groups, each of said 9-carbazolyl groups bonding to a respective one of the two terminals of the main chain.

4. The display apparatus as claimed in claim 3, wherein the main chain consists of from one to ten non-substituted 2,5-thiophenediyl groups, and
    the 9-carbazolyl groups are non-substituted 9-carbazolyl groups.

5. An electro-luminescent device comprising:
    (a) a substrate,
    (b) an anode,
    (c) a cathode, and
    (d) a luminous layer between the anode and the cathode, the luminous layer comprising a compound of the formula (1):

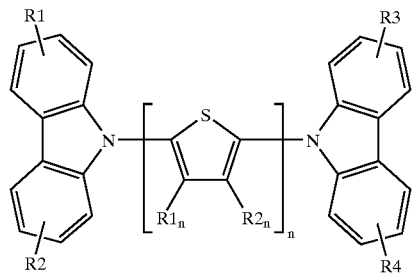

wherein n, including n in $R1_n$ and $R2_n$, is an integer from 1 to 10;
    $R1_n$ and $R2_n$ may each independently be a hydrogen atom; or a substituent selected from the group consisting of a linear or branched alkyl group that contains 1 to 20 carbon atoms, a cycloalkyl group that contains 3 to 10 carbon atoms, a linear or branched alkenyl group that contains 2 to 20 carbon atoms, a cycloalkenyl group that contains 3 to 10 atoms, a linear or branched alkynyl group that contains 2 to 20 atoms, a dienyl group that contains 4 to 20 carbon atoms, a linear or branched alkoxy group that contains 1 to 20 atoms, a hydroxyl group, a carboxyl group, an aldehyde group, a linear or branched acyl group that contains 2 to 20 carbon atoms, an amino group, a cyano group, a sulfonic group, a halogen group, a monocyclic or condensed polycyclic aryl group that contains 5 to 14 carbon atoms, and a heterocyclic group that contains at least one carbon atom and at least one hetero atom with a total number of carbon atoms and hetero atoms being 5 to 14; or $R1_n$ and $R2_n$ may form a ring that shares a bond between carbon atoms at the 3-position and 4-position of a 2,5-thiophenediyl group; and R1, R2, R3, and R4 may each independently be a hydrogen atom or a substituent selected from the group consisting of a linear or branched alkyl group that contains 1 to 20 carbon atoms, a cycloalkyl group that contains 3 to 10 carbon atoms, a linear or branched alkenyl group that contains 2 to 20 carbon atoms, a cycloalkenyl group that contains 3 to 10 carbon atoms, a linear or branched alkynyl group that contains 2 to 20 carbon atoms, a dienyl group that contains 4 to 20 carbon atoms, a linear or branched alkoxy group that contains 1 to 20 carbon atoms, a hydroxyl group, a carboxyl group, an aldehyde group, a linear or branched acyl group that contains 2 to 20 carbon atoms, an amino group, a cyano group, a sulfonic group, a halogen group, a monocyclic or condensed polycyclic aryl group that contains 5 to 14 carbon atoms, and a heterocyclic group that contains at least one carbon atom and at least one hetero atom with the total number of the carbon atoms and the hetero atoms being 5 to 14; or R1 and R2 and/or R3 and R4 may form a ring that shares a bond between adjacent carbon atoms of their respective 9-carbazolyl groups.

6. The electro-luminescent device as claimed in claim 5, wherein each $R1_n$ and $R2_n$ is a hydrogen atom.

7. The electro-luminescent device as claimed in claim 6, wherein each of R1, R2, R3 and R4 is a hydrogen atom.

* * * * *